United States Patent [19]

Seifert

[11] Patent Number: 4,813,586
[45] Date of Patent: Mar. 21, 1989

[54] SUTURE CLIP TONGS

[75] Inventor: Josef Seifert, Grosselfingen, Fed. Rep. of Germany

[73] Assignee: Helmut Diener, Tuttlingen, Fed. Rep. of Germany

[21] Appl. No.: 42,320

[22] Filed: Apr. 24, 1987

[30] Foreign Application Priority Data

May 7, 1986 [DE] Fed. Rep. of Germany ....... 3615405

[51] Int. Cl.⁴ .............................................. A61B 17/00
[52] U.S. Cl. ................................ 227/19; 227/DIG. 1; 227/120
[58] Field of Search .................... 227/19, DIG. 1, 120

[56] References Cited

U.S. PATENT DOCUMENTS

| 4,179,057 | 12/1979 | Becht | 227/DIG. 1 |
| 4,406,392 | 9/1983 | Campbell | 227/DIG. 1 |
| 4,491,133 | 1/1985 | Menges et al. | 227/120 X |
| 4,591,086 | 5/1986 | Campbell et al. | 227/120 X |

FOREIGN PATENT DOCUMENTS 0142225 5/1985 European Pat. Off. .

OTHER PUBLICATIONS

Proximate II Haut–Stapler (Ethicon).
Proximate Plus Haut–Stapler (Ethicon).

Primary Examiner—Paul A. Bell
Attorney, Agent, or Firm—Toren, McGeady & Associates

[57] ABSTRACT

Suture clip tongs include a main portion and a handle portion pivotably connected to the main portion. A magazine for suture clips is removably attached to the main portion. The magazine is formed by two sectional members which define a guide duct for the suture clips. When the magazine is being filled with the suture clips, the sectional members can be successively slid one into the other. This substantially facilitates filling and assembly of the magazine. The main portion of the tongs includes a bending mechanism for the suture clips. The magazine as well as the bending mechanism are reusable.

10 Claims, 2 Drawing Sheets

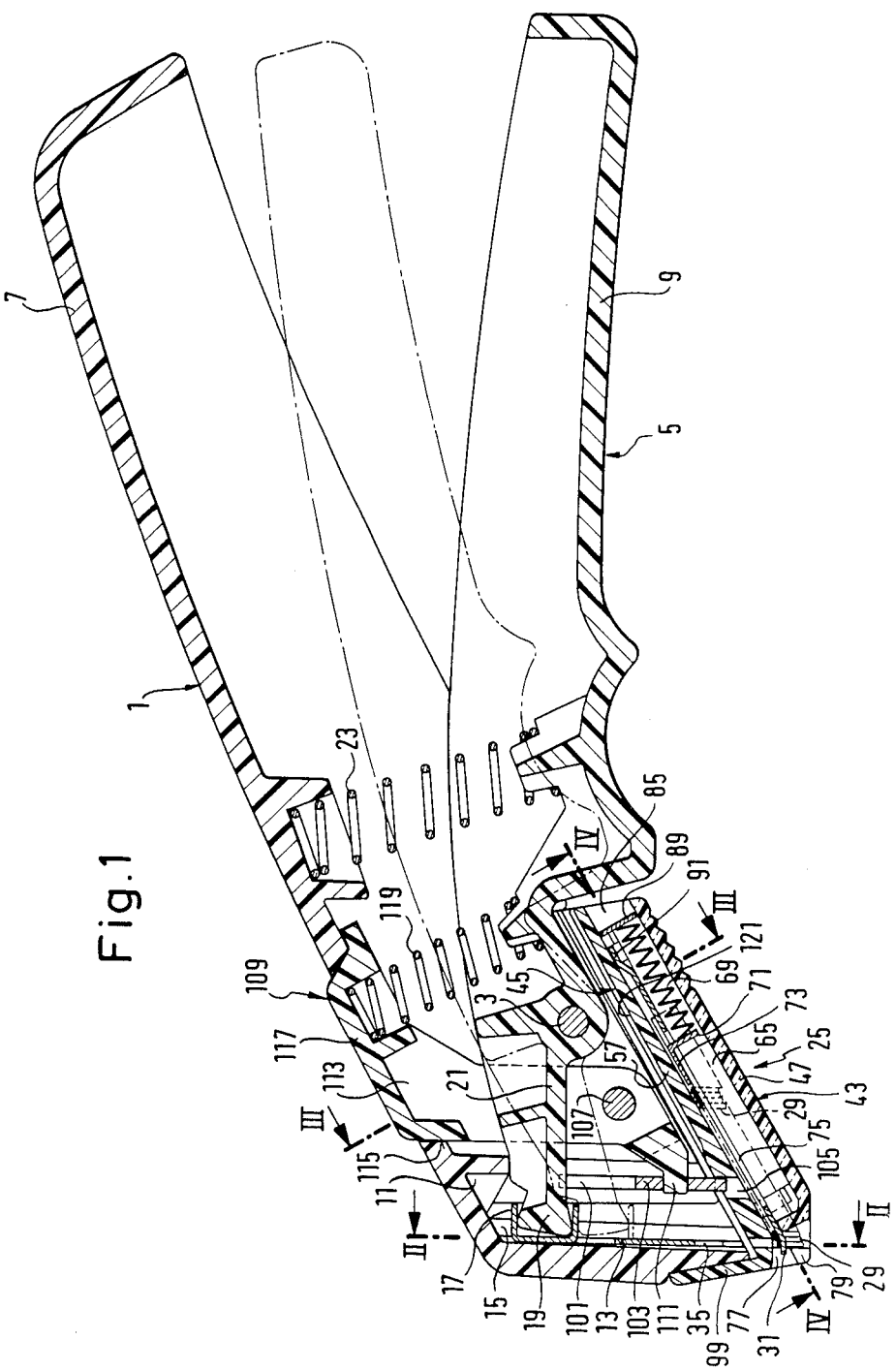

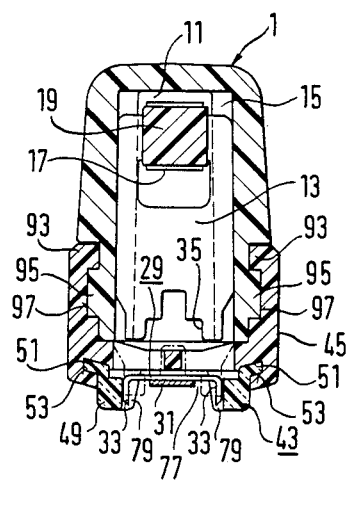
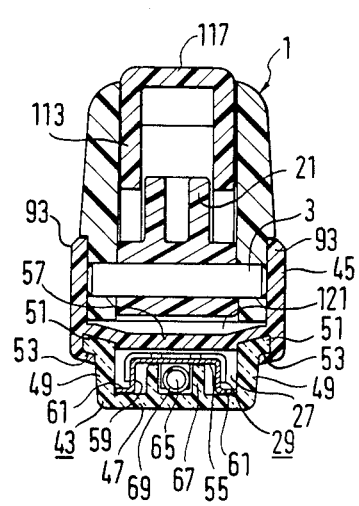
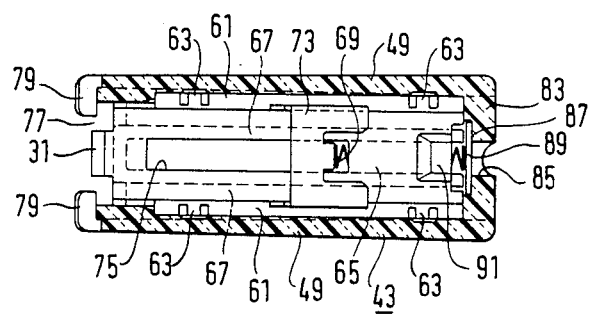
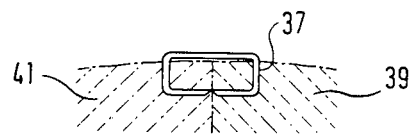

SUTURE CLIP TONGS

BACKGROUND OF THE INVENTION

1. Field of the Invention

The present invention relates to suture clip tongs or a surgical stapler having a main portion and a grip portion pivotally connected to the main portion. The main portion of the tongs includes a magazine composed of two sectional members which together form an elongated guide duct having an essentially U-shaped cross-section for a supply of essentially U-shaped suture clips or surgical staples. The magazine further includes a slide member slidable in the guide duct and a clip feed spring which biases the slide member toward a clip discharge opening of the guide duct. The tongs have a stop arranged in front of the clip discharge opening for limiting the delivery path of the clips. A clip bending mechanism actuated by the grip portion of the tongs includes an anvil arranged in the region of the clip discharge opening of the magazine and a bending die movably guided in the main portion of the tongs relative to the anvil.

2. Description of the Prior Art

Suture clip tongs of this type are known from European application No. 142 225. In these suture clip tongs, not only the bending die but also the anvil is mounted in the main portion of the tongs. The anvil forms the stop which prevents the unintentional discharge of suture clips at the clip discharge opening of the magazine. The magazine is not replaceable. As a result, the suture clip tongs cannot be reloaded during an operation once the supply of clips available in the magazine has been used up. A complete second pair of suture clip tongs must be available, so that several complete suture clip tongs must be sterilized after the operation. Moreover, the known suture clip tongs are structurally relatively complicated.

It is also known in the art to manufacture suture clip tongs which are used only once and are thrown away after use. However, this solution is relatively expensive because suture clips tongs of this type, even when designed for single use only, are relatively complicated.

It is, therefore, the primary object of the present invention to provide structurally simple suture clip tongs in which the magazine is replaceable during use, so that the suture clip tongs can be reloaded even during an operation with a new supply of suture clips. Furthermore, it is to be ensured that the magazine can be loaded with suture clips in a very simple manner.

SUMMARY OF THE INVENTION

In accordance with the present invention, in suture clip tongs of the type described above, the two sectional members of the magazine are connected to each other by slide-in connections extending in longitudinal direction of the guide duct, so that the slide-in connections fix the sectional members relative to each other in all directions transversely of the guide duct. In addition, the stop limiting the delivery path for the clips is formed as a part of the magazine. Also, the magazine together with the slide member and the clip feed spring are as a unit releasably mounted on the main portion of the tongs.

Several magazines filled with suture clips may be kept ready for an operation. These magazines can then be placed one after the other in the main portion of the suture clip tongs. The stop formed preferably by two projections or the like arranged on both sides of the clip discharge opening ensures even when the magazine is removed that the clip feed spring cannot push the clips out of the magazines. Since the sectional members can be inserted one into the other in longitudinal direction of the guide ducts, the magazine can be loaded with suture clips without problems even if the clips re available in loose form, i.e., are not connected to each other. The suture clips can be placed in one of the two sectional members and the other sectional member can then be slid successively over the suture clips already placed in the first sectional member. Thus, the suture clips cannot again fall out after they have been placed in the magazine.

The magazine may be a disposable magazine. In this case, after the magazine has been filled with suture clips, the two sectional members may advantageously be permanently connected to each other, for example, locked or glued to each other. However, the magazine is very well suited for reloading. In particular, the magazine can be easily and safely sterilized in the disassembled or partially open state.

In accordance with a preferred embodiment of the invention, a first of the two sectional members has an essentially U-shaped outer surface and closes with its bottom the magazine on the side facing away from the main portion of the tongs. Along its side walls projecting from its bottom towards the second of the two sectional members, the first sectional member is connected to the second sectional member by means of the slide-in connections.

An elongated, essentially U-shaped clip guiding member is placed in the first sectional member. This clip guiding member has a bottom part and side parts which extend from the bottom part toward the bottom of the first sectional member. The clip guiding member corresponds in its dimensions to the suture clips, so that the clips can be placed onto the clip guiding member with their legs facing the bottom of the sectional member. The bottom part of the clip guiding member and the second sectional member, on the one hand, and the side parts of the clip guiding member and the side walls of the first sectional member, on the other, are located spaced apart from each other and define the guide duct. The clip guide member and the bottom of the first sectional member, in turn, define a spring chamber in which the clip feed spring, preferably constructed as a helical compression spring, is accommodated in a space-saving manner. In this embodiment, the slide member has a projection which extends into the spring chamber through a slot formed in the clip guiding member.

The clip guiding member preferably is a bent sheet metal piece which at its end adjacent to the clip discharge opening has a lug which forms the anvil. At its other end, the clip guiding member has a support projection which extends above the level of the guide duct and rests against the second sectional member. This support projection serves to absorb the tilting moments which act on the anvil. To fasten the bent sheet metal piece to the first sectional member, the side walls of the bent sheet metal piece are provided with spring claws or the like.

The spring chamber is preferably constructed so as to be accessible through an opening formed in an end wall of the first sectional member, so that the clip feed spring can be inserted or replaced even after the bent sheet metal piece has been mounted. The clip feed spring rests against a locking piece which is inserted into a pocket after the clip feed spring has been inserted in the spring chamber. This pocket is formed in the first sectional member and is open toward the second sectional member.

The slide-in connections between the first and sectional members advantageously are rib and groove connections which extend preferably essentially over the entire length of the sectional members. It has been found particularly advantageous if two pairs of ribs and grooves are used which guide the two sectional members relative to each other in the manner of dovetail-type connections. The guide surfaces of the ribs and grooves preferably become narrow toward the clip discharge opening and, thus, the clamp fit between the two sectional members ensures that the two sectional members are not unintentionally separated from each other during use of the suture clip tongs.

The magazine can be locked into the main portion of the tongs in many different ways. A particularly simple exchange during operation is possible if one of the sectional members and the main portion of the tongs include additional slide-in connections extending essentially in longitudinal direction of the guide duct. These slide-in connections guide one of the sectional members so as to be fixed to the main portion of the tongs in all directions transversely of the guide duct. The magazine can be slid alongside one of these slide-in connections onto the main portion of the tongs. The magazine is subjected to exact guidance, on the other hand, in the direction of impact of the bending die. For fixing the magazine in the direction of the slide-in connections, particularly suitable is a locking unit composed of a locking pawl provided on the main portion of the tongs and a recess in one of the sectional members. This is particularly true when the locking pawl can be released by a push button arranged easily accessible on the main portion of the tongs.

The various features of novelty which characterize the invention are pointed out with particularity in the claims annexed to and forming a part of this disclosure. For a better understanding of the invention, its operating advantages and specific objects attained by its use, reference should be had to the drawings and descriptive matter in which there is illustrated and described a preferred embodiment of the invention.

BRIEF DESCRIPTION OF THE DRAWINGS

In the drawing:

FIG. 1 is a longitudinal sectional view of suture clip tongs according to the present invention;

FIG. 2 is a transverse sectional view of the tongs of FIG. 1, taken along sectional line II—II;

FIG. 3 is a transverse sectional view of the tongs of FIG. 1, taken along sectional line III—III;

FIG. 4 is a transverse sectional view of the magazine of the tongs of FIG. 1, taken along sectional line IV—IV; and FIG. 5 is a schematic illustration of a suture clip which has been bent by means of the suture clip tongs of FIG. 1.

DETAILED DESCRIPTION OF THE INVENTION

As illustrated in FIGS. 1–4, the suture clip tongs according to the present invention include an essentially dish-shaped main portion 1. A grip portion 5 is connected to main portion 1 so as to be pivotable about an axis 3. Main portion 1 has an essentially elongated shape and forms on one side of axis 3 a handle 7 which is located opposite a handle 9 of grip portion 5. The main portion 1 forms on the opposite side of the axis 3 a chamber 11 in which a bending die is guided in a guide 15 so as to be slidable transversely of the longitudinal direction of main portion 1. Bending die 13 has a sliding bracket 17 which is engaged by a sliding block 19 provided at the free end of an arm 21 of grip portion 5 located opposite handle 9. A helical compression spring 23 guided between handles 7 and 9 maintains bending die 13 in a position in which it is retracted in chamber 11 and from which it can be pushed out by pressing handles 7 and 9 together.

A magazine 25 is replaceably mounted in main portion 1. Magazine 25 faces the outlet end of bending die 13 and encloses an elongated guide duct 27 which is essentially U-shaped in cross-section, as can be seen in FIG. 3. A supply of loose, essentially U-shaped suture clips 29 is placed in a row in longitudinal direction of guide duct 27. The magazine includes an anvil 31 whose width is smaller than the length of the base of each suture clip 29, so that the legs 33 of the suture clips extend on both sides beyond anvil 31 and are being bent by a bending recess 35 into a suture clip ring 37. The recess 35 is formed on the end face of the bending die 13 facing the anvil and has a size which corresponds to the width of the anvil and takes into consideration the thickness of the suture clips 29. The resulting suture clip ring 37 clamps the wound halves 39 and 41 together, as illustrated in FIG. 5.

Magazine 25 is mounted on main portion 1 so as to be replaceable as a unit. The magazine 25 includes two elongated sectional members 43 and 45 which enclose guide duct 27. Sectional member 43 has an essentially U-shaped outer surface as seen in cross-section. Sectional member 43 has a bottom wall 47 and two side walls 49 which project from bottom wall 47 toward sectional member 45. The free longitudinally extending edges of the side walls 49 have longitudinally extending ribs 51 which extend in longitudinal direction of guide duct 27 and face away from each other. Longitudinal ribs 51 engage in the manner of a dovetail-guide connection in complementary longitudinal grooves 53 provided in the other sectional member 45. The longitudinal ribs 51 and longitudinal grooves 53 form slide-in connections which serve to slidably guide the sectional member 43 in sectional member 45. These slide-in connections fix the two sectional members 43 and 45 transversely of the longitudinal direction thereof.

An essentially U-shaped clip guiding member 55 constructed as a bent sheet metal piece is placed in sectional member 43. The outer dimensions of clip guiding member 55 correspond to the inner dimensions of suture clips 29. Guide duct 27 is formed by the clip guiding member 55 together with a transverse wall 57 of sectional member 45 connecting grooves 53, on the one hand, and the side walls 49 of sectional member 43, on the other. The free longitudinal edges of side walls 59 of clip guiding member 55 have flanges 61 which face away from each other. As can best be seen in FIG. 4, these flanges 61 are punched to form tongues 63 which are clawed together with side walls 49 of sectional member 43 and, thus, hold clip guiding member 55 in sectional member 43.

The space surrounded by the interior of the clip guiding member 55 and the bottom wall 47 forms spring chamber 65 in which, guided by ribs 67, a helical compression spring 69 is arranged which acts in longitudinal direction of guide duct 27. Spring 69 rests in a lug 71 of a slide member 73 which is mounted so as to be longitudinally slidable on clip guiding member 55 in guide duct 27. Lug 71 extends into spring chamber 65 through a longitudinal slot formed in clip guiding member 55.

Spring 69 presses the suture clips 29 in direction toward a discharge opening 77 which annularly surrounds anvil 31. Projections 79 are arranged in front of discharge openings 77 projecting from side walls 49 towards the anvil. Projections 79 limit the delivery path of the clips 29.

The end of sectional member 43 opposite anvil 31 is closed by an end wall 83 which defines an inlet opening 85 for spring 69. Inlet opening 85 is flush with spring chamber 65. End wall 83 forms a pocket 87 in which a locking piece 89 can be inserted when sectional member 45 is removed and against which spring 69 rests with its end opposite slide member 73. Clip guiding member 55 has at its end opposite anvil 31 an embossed portion 91 facing transverse wall 57 of sectional member 45. Portion 11 serves to secure the clip guiding member 55 against tilting when pressure is applied to anvil 31.

Magazine 25 is assembled as follows. Clip guiding member 55 is initially placed in the sectional member 43 as illustrated, so that tongues 63 are clawed into side walls 49. Subsequently, the suture clips 29 are placed on clip guiding member 55 and the sectional member 45 is successively slid onto sectional member 43, so that the already inserted clips cannot fall out or be displaced. Slide member 73 is inserted and sectional member 45 is pushed close to pocket 87 in order to fix slide member 73. Spring 69 is now inserted through inlet opening 85 and is tensioned until it is close to pocket 87 by means of a tool, for example a screwdriver or the like. Locking piece 89 is now placed in pocket 87. Finally, the sectional members 43 and 45 are completely slid into each other. As indicated in FIGS. 2-4, the guide surfaces of longitudinal ribs 51 and grooves 53 converge toward each other, so that the sectional member 43 is fixed in a tight fit toward discharge opening 77.

The sectional member 45 is used to attach magazine 25 to main portion 1. On the side of transverse wall 57 facing main portion 1, sectional member 45 has flanges 23 which partially enclose main portion 1. Ribs 95 extending in longitudinal direction of guide duct 27 are provided in main portion 1. These ribs 95 engage in complementary longitudinal grooves 97 of flanges 93. Accordingly, sectional member 45 and, thus, magazine 25, can be slid onto main portion 1. Adjacent clip discharge opening 77, the flanges 93 are connected to each other by means of an end wall 99 which limits the path of insertion of magazine 25.

For locking magazine 25 to main portion 1, a plate-like pawl 103 is slidably guided in grooves 101 of chamber 11. Pawl 103 engages an opening 105 of transverse wall 57 and locks magazine 25 when fully engaged in opening 105. A double-arm actuating lever 109 which is swivelably mounted about an axle 107 on main portion 1 engages with a first arm 111 into pawl 103 and has on its second arm 113 an actuating push button 117 which extends through the opening 115 on the side of main portion 1 facing away from magazine 25. A helical compression spring 119 mounted between arm 113 and handle 9 of grip portion 5 pretensions pawl 103 in locking direction and, since it acts in the same direction as spring 23, also acts in opening direction of the tongs.

Thus, spring 23 may be of weaker strength than would be necessary without spring 119.

Magazine 25 is placed on longitudinal ribs 95 on the end of main portion 1 facing away from handle 7. Outer surface 121 of transverse wall 57 facing pawl 103 is shaped as an inclined surface for insertion along which pawl 103 is automatically engaged with opening 105. Magazine 25 is released by pressing push button 117, so that magazine 25 can be freely pulled out.

Main portion 1 and grip portion 5 of the tongs, lever 109 and sectional members 43 and 45 are made of injection molded plastics material which can be sterilized. It is advantageous if sectional member 43 is made of a transparent plastics material, so that it is possible to determine the number of suture clips still in the magazine from the outside. Bending die 13, clip guiding member 55 and pawl 103 are preferably made of stainless steel.

While a specific embodiment of the invention has been shown and described in detail to illustrate the application of the inventive principles, it will be understood that the invention may be embodied otherwise without departing from such principles.

I claim:
1. Suture clip tongs, comprising
   (a) a main portion;
   (b) a magazine for a supply of essentially U-shaped suture clips, the magazine fastened to the main portion so as to be releasable therefrom as a unit, the magazine having
      a first elongated sectional member having an essentially U-shaped cross-section, the first sectional member having on a side facing away from the main portion a bottom for closing the magazine and side walls connected to the bottom,
      an elongated clip guiding member placed in the first sectional member, the guiding member being a bent sheet metal part of essentially U-shaped cross-section, the clip guiding member having a bottom part and side parts projecting from the bottom part toward the bottom of the first sectional member,
      a second elongated sectional member attached to the first sectional member, the first and second sectional members and the clip guiding member forming an elongated, essentially U-shaped guide duct, the guide duct defined on one side by the second sectional member and the bottom of the clip guiding member spaced apart from the second sectional member and on the other side by the side walls of the first sectional member and the side parts of the clip guiding member extending spaced apart from the side walls, an end of the guide duct defining a clip discharge opening,
      a slide member slidably placed in the guide duct,
      a clip feed spring biasing the slide member toward the clip discharge opening,
      stop means arranged in front of the discharge opening for limiting the delivery of clips out of the guide duct;
   (c) a clip bending mechanism, including
      an anvil adjacent the clip discharge opening, the anvil being a lug formed integrally in one piece with the clip guiding member of the magazine,
      a bending die movably guided in the main portion relative to the anvil and independently of the magazine;

(d) a handle portion pivotally connected to the main portion for actuating the clip bending mechanism.

2. The suture clip tongs according to claim 1, comprising two slide-in connections for fixing together the first and second sectional members of the magazine transversely of the guide duct, each of the slide-in connections defining a groove extending essentially over the entire length of one of the sectional members and a rib extending in longitudinal direction on the other sectional member, the grooves and the ribs defining guide surfaces which converge toward each other in longitudinal direction toward the clip discharge opening.

3. The suture clip tongs according to claim 1 wherein the clip feed spring is arranged in a spring chamber defined by the clip guiding member and the bottom of the first sectional member, and wherein the clip guiding member defines a slot extending in longitudinal direction, the slide member having a projection, the projection extending through the slot into the spring chamber.

4. The suture clip tongs according to claim 3, wherein the first sectional member includes an end wall for closing off the end of the guide duct opposite the clip discharge opening, the end wall defining an opening for permitting insertion of the clip feed spring into the spring chamber, the end wall defining a pocket which is open toward the second sectional member, a locking piece inserted in the pocket, the locking piece closing the opening and supporting the clip feed spring.

5. The suture clip tongs according to claim 3, wherein the clip guiding member has two ends, the clip guiding member supporting at the end adjacent the clip discharge opening the lug forming the anvil and at the other end a support projection projecting toward the second sectional member.

6. The suture clip tongs according to claim 5, wherein the side parts of the clip guiding member facing away from the bottom part have longitudinal edges, flanges attached to the longitudinal edges, the flanges resting against the side walls of the first sectional member, and spring claws punched into the flanges.

7. The suture clip tongs according to claim 1, comprising additional slide-in connections formed in one of the sectional members and the main portion, the additional slide-in connection extending in longitudinal direction of the guide duct and guiding the one sectional member onto the main portion fixed in all directions transversely of the guide duct.

8. The suture clip tongs according to claim 7, wherein one of the sectional members defines a locking opening and a locking pawl is movably guided on the main portion, a locking spring biasing the locking pawl in a direction toward engagement with the locking opening.

9. The suture clip tongs according to claim 8, comprising a double-arm lever mounted in the main portion, the lever swivelable about an axis parallel to the pivoting axis of the grip portion, a first arm of the lever connected to the locking pawl and a second arm of the lever forming an actuating push button extending through a cutout defined in the main portion.

10. The suture clip tongs according to claim 9, wherein the locking spring is tensioned between the second arm and the grip portion, and the locking spring biases the grip portion in opening direction of the tongs.

* * * * *